United States Patent [19]

Turner

[11] Patent Number: 5,643,233

[45] Date of Patent: Jul. 1, 1997

[54] POST-SURGICAL DRAINAGE CONTAINER CARRIER

[76] Inventor: Nancy F. Turner, 203 Deerfield Dr., Greer, S.C. 29650

[21] Appl. No.: 551,566

[22] Filed: Nov. 1, 1995

[51] Int. Cl.[6] .................................. A61F 5/44; A45F 5/00
[52] U.S. Cl. .......................... 604/332; 224/663; 224/677; 604/345
[58] Field of Search ................................. 604/317, 332, 604/337, 345, 346, 347, 349, 353; 224/253, 252, 224, 226

[56] References Cited

U.S. PATENT DOCUMENTS

| | | | |
|---|---|---|---|
| 2,699,782 | 1/1955 | Chester | 128/295 |
| 4,548,375 | 10/1985 | Moss | 248/205.2 |
| 4,923,105 | 5/1990 | Snyder | 224/253 |
| 5,026,362 | 6/1991 | Willett | 604/345 |
| 5,032,118 | 7/1991 | Mason | 604/349 |
| 5,135,519 | 8/1992 | Helmer | 604/332 |
| 5,259,541 | 11/1993 | Reese | 224/226 |

*Primary Examiner*—John G. Weiss
*Assistant Examiner*—David J. Cho
*Attorney, Agent, or Firm*—Gerald R. Boss; Cort Flint

[57] ABSTRACT

A post-surgical drainage carrier for carrying a post-surgical drainage container used for draining fluids from patients after surgery. The post-surgical drainage carrier includes a pouch and a belt. The pouch includes a front pouch sidewall and a back pouch sidewall. The front pouch sidewall terminates at a pouch lip which is interconnected with a pouch extension at first and second lip attachment points which may extend downwardly and inwardly to open a pouch mouth for easily placing the drainage container within the pouch interior.

4 Claims, 4 Drawing Sheets

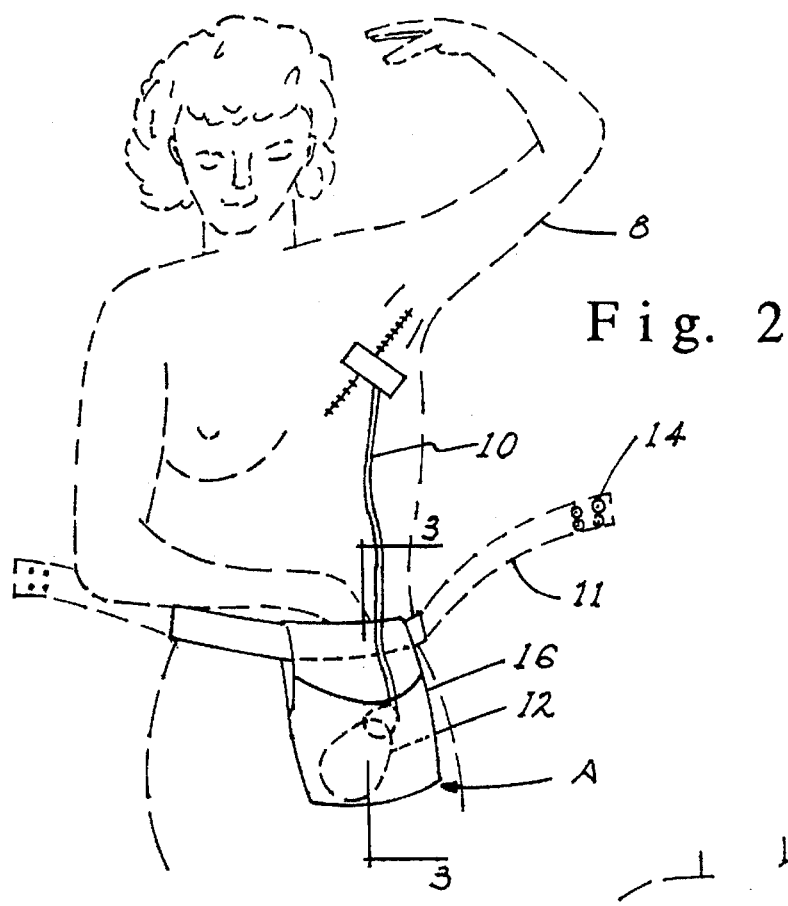
Fig. 2
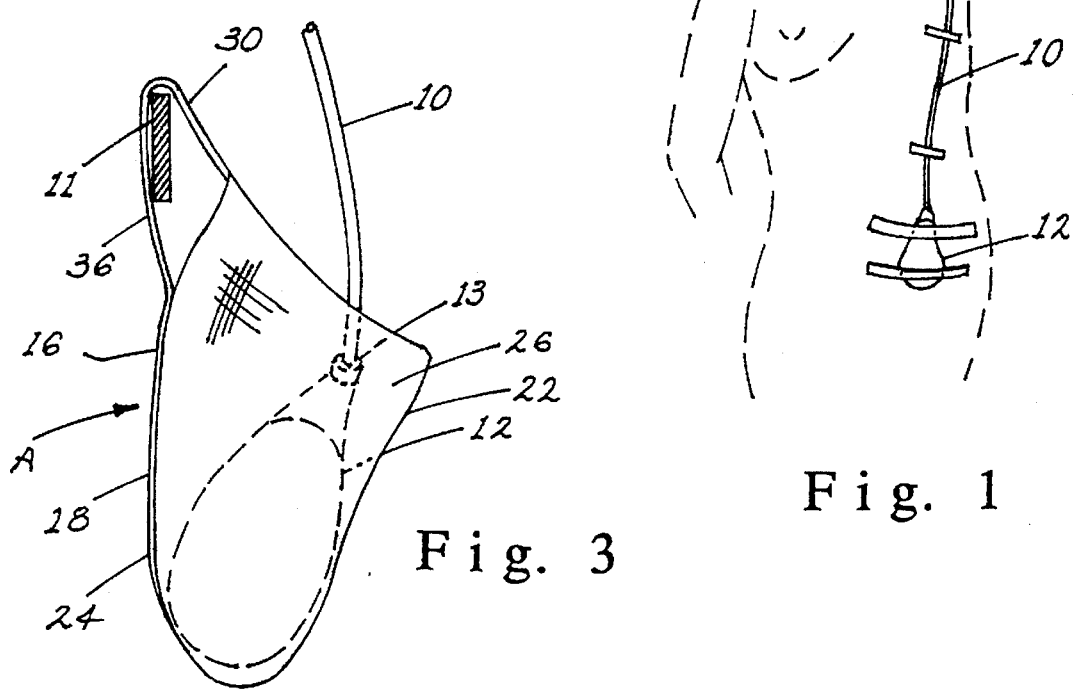
Fig. 3
Fig. 1

POST-SURGICAL DRAINAGE CONTAINER CARRIER

BACKGROUND OF THE INVENTION

This invention relates to a carrier to be worn around the waist of an individual, and particularly, to a light-weight, comfortable carrier specifically designed for carrying a post-surgical drainage container which is used to contain bodily fluids generally after major surgery such as mastectomies.

Major surgery such as cardiovascular operations and mastectomies are very traumatic to the human body. Consequently, after surgery, the lymph nodes of the body generally secrete an excessive amount of fluids. In order to assist in the drainage of these excessive fluids, drainage tubes are connected with the lymph nodes and other parts of the body for draining the fluid away from the body to prevent swelling. Drainage containers are attached to the tubes for receiving the fluid. Generally however, the tubes and containers are merely taped to the individual and are required to be worn for at least a week. Since the containers must be untaped and drained, the tape looses its general adhesiveness. Accordingly, during the week, the tape usually comes undone at inopportune times and the weight of the fluid in the container pulls on the tubes causing pain. This is especially so, when the patient is taking a shower and the water loosens the tape.

In order to alleviate this problem, some people wear undergarments when taking a shower and place the container in an unorthodox, uncomfortable position by placing the container in the undergarment. Also, during daily wear, these people continue to maintain the container within their undergarments or tuck them between the pants and the undergarments. Positioning of the drainage containers within the undergarments is very uncomfortable and hinders the movement of the already discomforted patient. Thus, there is a need to carry the drainage container in a suspended state which may consistently support the container in a comfortable manner providing the patient with freedom of movement while also providing access to the drainage container.

Bags to be worn around the waist for carrying objects have been designed for containing various items. U.S. Pat. No. 4,974,761 discloses a slot bag which is designed to include a closable pouch which may be worn around the waist of a person in order to transport a coin cup. Also, U.S. Pat. No. 5,259,541 discloses a belt with an attached bag specifically adapted for holding tennis balls while playing tennis.

Bag holders have also been developed for the medical field. U.S. Pat. No. 5,026,362 discloses an ostomy bag holder and cover which is specifically designed to carry an ostomy bag. U.S. Pat. No. 2,699,782 discloses a bed-type urinal which is designed to be carried around the waist of an individual, specifically a male, which is designed to carry an absorbent pad for absorbing the urine of the patient. The bed-type urinal is specifically designed to receive the male organs and utilizes a belt, anchoring tape, and a pair of auxiliary tapes which cooperate for attaching and supporting the bag with respect to the male organ.

While each of these bags fulfil specific functions, none of them are designed to specifically and comfortably hold a post-surgery drainage container in a manner which makes the post-surgery drainage container easily accessible for removing and draining when necessary while also supporting the container preventing the container from tugging on the drainage tubes.

Accordingly, it is an object of the present invention to provide a post-surgery drainage container carrier which is designed to carry a post-surgery drainage container;

Yet another object of the present invention is to provide a post-surgery drainage container carrier which supports the post-surgery drainage container and provides easy access to the container for removing the container to drain;

Another object of the present invention is to provide a post-surgery drainage container carrier which is comfortable to wear and is washable.

SUMMARY OF THE INVENTION

The above objectives are accomplished according to the present invention by providing a post-surgical drainage carrier for carrying a post-surgical drainage container connected to tubes which are interconnected to a patient for draining bodily fluids. The post-surgical drainage carrier includes a light-weight belt of sufficient length for encircling the patient and a pouch having a pouch interior for receiving and suspending the post-surgical drainage container preventing the container from pulling on the tubes. The pouch includes a front pouch sidewall and a back pouch sidewall which are interconnected for defining the pouch interior. The back pouch sidewall includes a generally vertical pouch extension which extends above the front pouch sidewall. The front pouch sidewall terminates at a pouch lip which is interconnected with the pouch extension at a first and second attachment point. A belt attachment means attaches the pouch to the belt. The first and second lip attachment points are located beneath the belt so that the pouch lip may deform outwardly. A pouch mouth is defined by the pouch extension and the pouch lip communicating with the pouch interior. The pouch mouth has a first position which is generally closed defined by the pouch lip extending parallel across the lower portion of the pouch extension. In this position, the pouch extension extends generally vertical above the front pouch sidewall.

The pouch mouth has a second position wherein the pouch lip extends outwardly away from the patient moving the first and second lip attachment points downward and towards each other deforming the pouch extension from the generally vertical position to a generally oblique angular position. The deformed pouch extension extends the front pouch sidewall away from the patient so that the open pouch mouth fully exposes the pouch interior providing easy access for placing the drainage container within the pouch interior. The front pouch sidewall, pouch lip and pouch extension being made from a soft, pliable material enabling the pouch mouth to be opened to the second position.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein:

FIG. 1 shows the current method of carrying a post-surgery drainage container by taping the container to the patient;

FIG. 2 illustrates a post-surgical drainage container being carried by a post-surgical drainage container carrier constructed according to the present invention; and FIG. 3 is a sectional view of the post-surgical drainage container carrier taken along line 3—3 illustrating the expansion of the pouch's mouth providing easy access to the post-surgical drainage container according to the invention;

DESCRIPTION OF A PREFERRED EMBODIMENT

Figure 4:
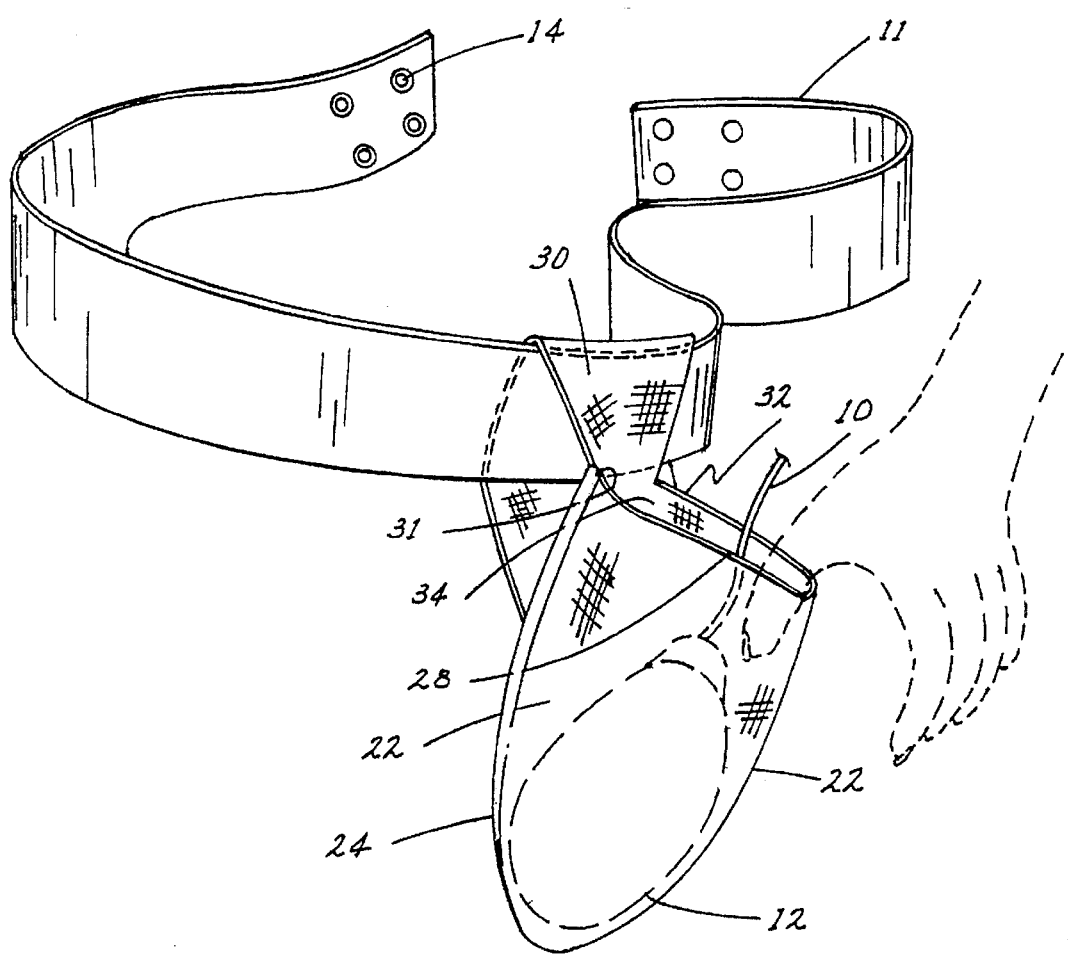
FIG. 4 is a prospective view illustrating the expansion of the pouch mouth for placing a post-surgical container within the pouch interior according to the invention.

Referring now in more detail to the drawings, the invention will now be described in more detail. As illustrated in FIGS. 1 and 2, after major surgery such as a mastectomy, drainage tubes 10 are attached to lymph nodes of the patient. Usually after major surgery, the body excretes an excessive amount of bodily fluids and it is necessary to drain these fluids to prevent the body from swelling. The drainage tubes are placed within the body cavity and the skin is stitched up along the surgical cut and around the drainage tubes. Post-surgical drainage container 12 having connectors 13 is attached to the ends of drainage tubes 10 for receiving the bodily fluids. In the preferred embodiment, post-surgical drainage container 12 is manufactured by the company Heyer Schulte as is known in the medical field and has an elliptical shape approximately four inches in length and two inches in width for holding approximately one hundred and twenty-five cubic centimeters of bodily fluids.

As shown in FIG. 1, generally drainage tubes 10 and post-surgical drainage container 12 are taped to the patient. The problem associated with this method is that the tubes are generally maintained within the patient for a period of seven to fourteen days. During this time, the tape loosens and drainage container 12 is left unsupported. As drainage container 12 fills up with bodily fluids container 12 pulls on the drainage tubes causing pain for the patient. The tape loosens for several reasons such as the tape loosing its general adhesiveness. Taking showers is very problematic because the water loosens the tape during showering while the patient is standing, thus leaving drainage container 12 unsupported and exposing the patient to the risk that the container may drop at any time pulling drainage tubes 10 from the body.

As shown in FIG. 2, drainage container carrier A is designed for carrying post-surgical drainage container 12 in a suspended position thereby removing any tension along tube 10 preventing tube 10 from pulling on the patient. Drainage container 12 includes connectors 13 for connecting tube 10 to drainage container 12 enabling fluid to flow from tube 10 and be collected in drainage container 12. Drainage container holder A includes belt 11 and drainage container carrier 16. Belt 11 is of sufficient length to wrap around the waist of patient 8 and is preferably made from terry cloth having an elastic component for stretching. Releasable attachment means 14 provide belt 11 with multiple attachment lengths for compensating in the different waist sizes of the patients. Releasable attachment means 14 are attached to opposite ends of belt for securing the belt around the waist of the person. Releasable attachment means 14 is preferably snaps but may also be VELCRO® or a buckle.

As shown in FIGS. 3, 4, 5 and 6, drainage container carrier 16 receives drainage container 12 and supports drainage container 12 in an upright position enabling fluid to flow from tube 10 to drainage container 12. Drainage container carrier 16 includes pouch 18 and belt attachment means 20 for carrying drainage container carrier 16 with belt 11. Belt attachment means 20 is preferably a loop but may also be VELCRO®.

Pouch 18 includes front pouch sidewall 22 and back pouch sidewall 24. In the preferred embodiment, front pouch sidewall 22 and back pouch sidewall 24 are constructed from a unitary piece of terry cloth of ten percent weight for softness and pliability. Front pouch sidewall 22 and back pouch sidewall 24 are sewn together along their sides providing pouch 18 with pouch interior 26. Front pouch sidewall 22 is folded over and sewn onto itself to define front pouch lip 28.

Figure 5:
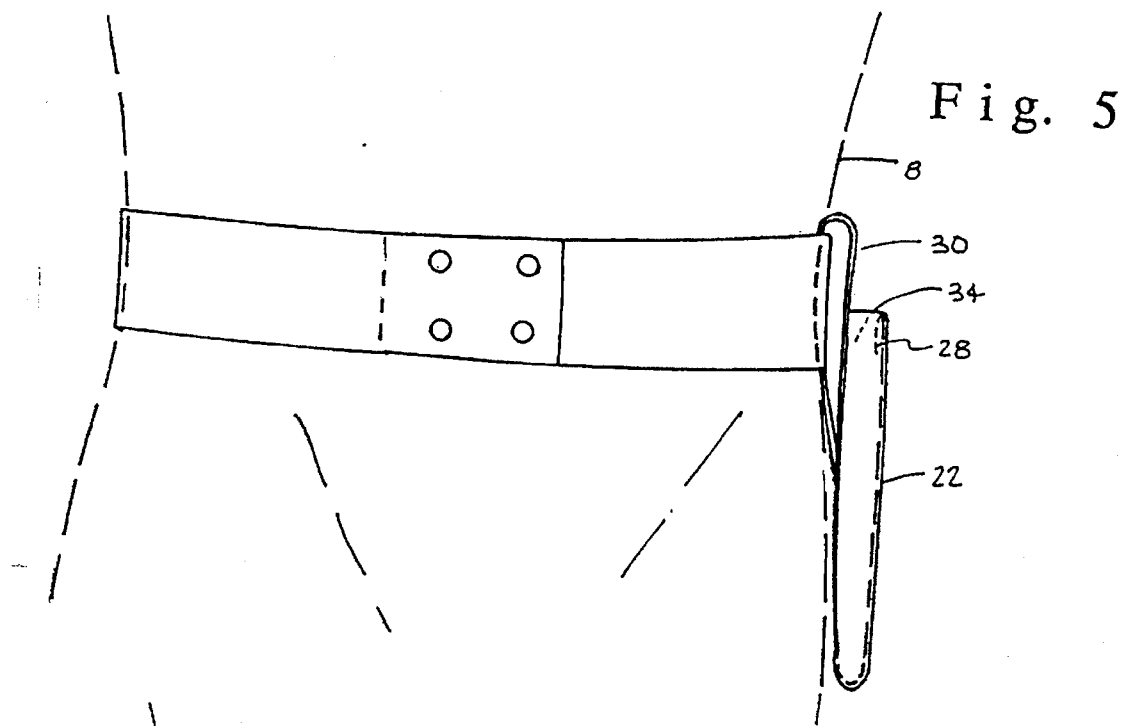
FIG. 5 is a side view illustrating the post-surgical drainage container carrier in a position without a post-surgical drainage container.
Figure 8:
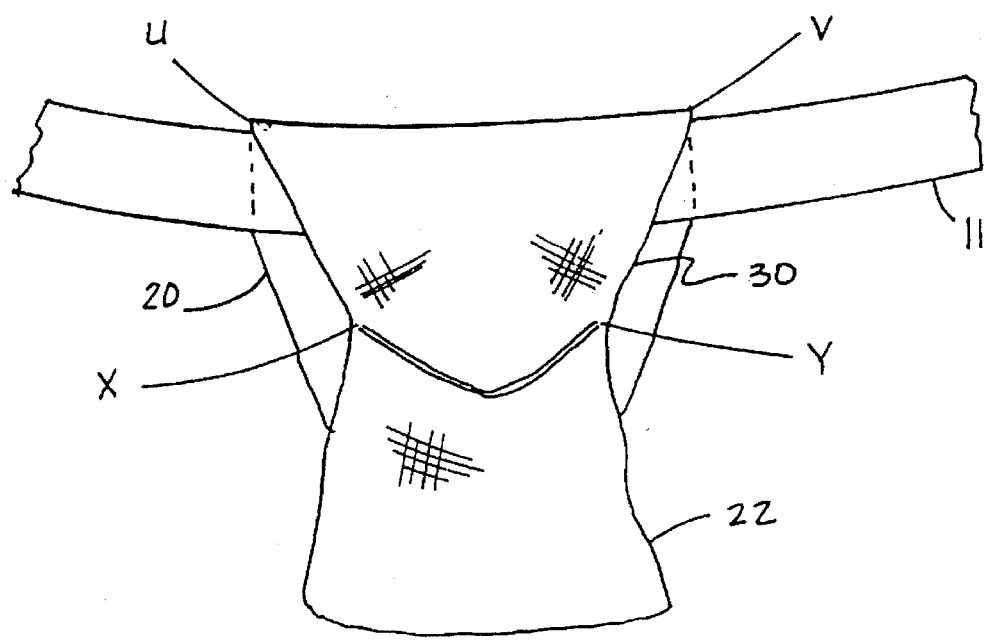
FIG. 8 is a frontal prospective view illustrating the pouch extension portion of the post-surgical drainage container carrier in an extended position according to the invention for expanding the pouch mouth.

Back pouch sidewall 24 extends above front pouch lip 28 defining pouch extension 30. Front pouch lip 28 is attached to pouch extension 30 at first front pouch lip end 31 and second front pouch lip end 32. The attachment points of first front pouch lip end 31 and second front pouch lip end 32 are important to the invention and are designated as attachment point X and attachment point Y respectively. Pouch mouth 34 is defined by the offset of front pouch lip 28 from pouch extension 30. As shown in FIG. 5, pouch mouth 34 has a first position where front pouch lip 28 runs parallel across the lower portion of pouch extension 30. In the preferred embodiment, back pouch sidewall 24 is folded over and sewn to define belt loop 36 for receiving belt 11. As shown in FIGS. 3, 4 and 8, belt 11 is smaller in height than pouch extension 30 so that attachment points X and Y will not be restricted in movement when belt loop 36 receives belt 11.

As shown in FIGS. 2, 4, 6, 7 and 8, the inclusion of pouch extension 30 is important to the invention and enables pouch mouth 34 to extend a sufficient distance away from patient 8 so that pouch mouth 34 fully exposes pouch interior 26 providing easy access for placing drainage container 12 within pouch interior 26.

Figure 7:
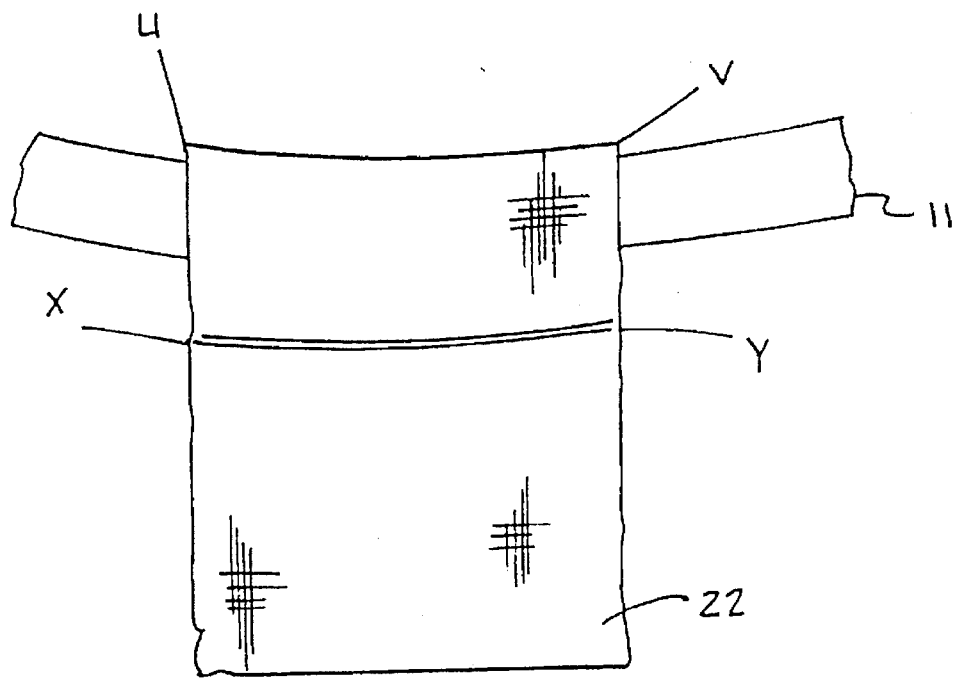
FIG. 7 is a frontal prospective view illustrating pouch extension portion of the post-surgical drainage container carrier in a non-extended position according to the invention.

As shown in FIGS. 7 and 8, with belt 11 supporting the upper portion of belt loop 36 at belt attachment points U and V, attachment points X and Y are suspended beneath belt 11 and may flex outwardly away from patient 8 and inwardly towards each other for elongating pouch mouth 34. The inventor has found that if belt 11 were attached directly to the back pouch sidewall parallel to the front sidewall and no pouch extension was present, then the points at which the front sidewall connected with the back sidewall would be fixed restricting the opening of the pouch mouth.

Figure 6:
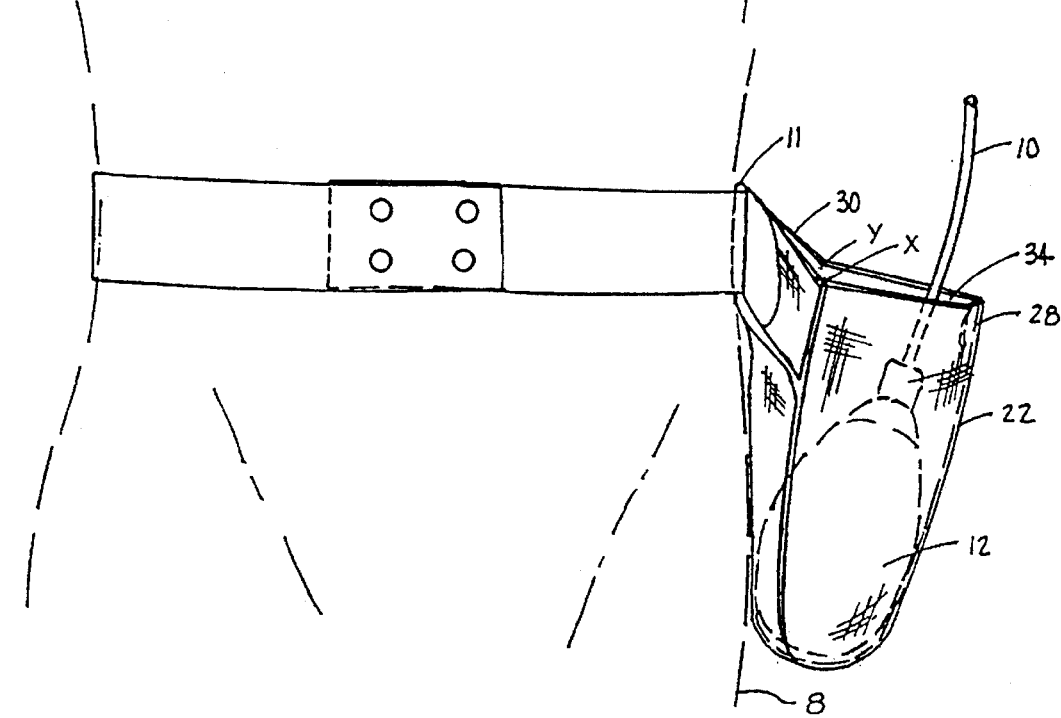
FIG. 6 is a prospective view illustrating a post-surgical container being carried by a post surgical drainage container carrier according to the invention.

As shown in FIGS. 4, 6, and 8, in order to facilitate the placement of drainage container 12 within pouch interior 26, front pouch lip 28 is moved outwardly away from the patient so that pouch mouth 34 has a second position. When front pouch lip 28 is moved away from patient 8, pouch extension 30 deflects from a generally vertical position to a generally oblique angular position and attachment points X and Y deform downward and towards each other enabling pouch mouth 34 to be opened to a readily applicable distance providing access to pouch interior 26 for easily placing post drainage container 12 within pouch interior 26. It is important that pouch mouth 34 be sufficiently opened because room must be made available to comfortably fit drainage tube 10 within pouch mouth 34. By suspending front pouch lip 28 at attachment points X and Y, pouch mouth 34 can obtain a larger profile than if attachment points X and Y were fixed at the point where belt 11 carries pouch 18. It is desired that belt attachment points U and V remain at a fixed location when front pouch lip 28 is extended outward, but some bunching may occur.

Furthermore, as shown in FIGS. 3, 4, 6 and 8, with belt 11 being of a less height than pouch extension 30, when belt 11 carries post-surgical container carrier 16, the dimensions of both pouch extension 30 and front pouch lip 28 may be utilized for defining pouch mouth 34 exposing the full pouch interior 26. With belt 11 carrying carrier 12 at belt attachment points U and V, belt extension 30 may deflect outwardly from patient 8 thereby widening pouch mouth 34.

As shown in FIGS. 3 and 6, the weight of the fluids draining into drainage container pushes against front pouch wall 22 pulling front pouch lip 28 away from back pouch wall 24. In this manner, front pouch lip 28 extends outward into an arcuate profile for easy access to drainage container 12. Also, in the preferred embodiment, pouch 18 is six inches wide and six inches high with pouch extension 30 being one point five inches high. With extension 30, front pouch sidewall 22 may extend a length greater than its width away from belt 11 for providing a wide pouch mouth.

In the preferred embodiment, post surgical drainage carrier is made from terry cloth of 10 percent weight. The terry cloth is light-weight, comfortable to the patient's skin and is also washable and easily dried. As previously mentioned, the taking of showers is difficult with the post surgical drainage containers because the person is standing upright and the containers pull on the tubes causing discomfort. With this material the patient can wear the carrier during the shower, and after the shower can easily remove the drainage container and replace the post-surgical drainage container holder with a second one so that the first one may be washed and then dried.

Also, by providing a loop as belt attachment means 20, the holder may be positioned anywhere along the belt depending on where the drainage container is connected. This versatility ensures that any drainage container associated with any surgery may be easily carried.

Therefore, it can be seen that an advantageous post-surgical container holder may be had according to the invention. After surgery, the patient is very sore and has limited movement. Post-surgical drainage containers need to be emptied frequently and solely using tape to secure the containers does not provide for a secure fit. The carrying of the container by a pouch which extends to a width for easy access to the pouch's interior facilitates in the supporting and removal of the drainage container for draining. The use of an pouch extension assists in providing a pouch mouth which easily expands into the pouch interior.

While a preferred embodiment of the invention has been described using specific terms, such description is for illustrative purposes only, and it is to be understood that changes and variations may be made without departing from the spirit or scope of the following claims.

What is claimed is:

1. A post-surgical drainage system for draining bodily fluids from a patient after surgery, said drainage system comprising:
   a drainage tube connectable to said patient for draining said bodily fluids away from said patient;
   a post-surgical drainage container having connectors connecting to said drainage tube for receiving said bodily fluids;
   a light-weight, washable post-surgical drainage container carrier for carrying said post-surgical drainage container at a position beneath said drainage tube enabling said bodily fluids to flow into said post-surgical drainage container;
   a pouch having a pouch interior included in said post-surgical drainage container carrier for receiving and supporting said post-surgical drainage container preventing said drainage container from pulling on said drainage tube;
   a front pouch sidewall and back pouch sidewall included in said pouch for defining said pouch interior;
   said back pouch sidewall extending above said front pouch sidewall defining a pouch extension;
   an open pouch mouth defined by said front pouch sidewall and said pouch extension, said open pouch mouth communicating with said pouch interior;
   said front pouch sidewall being made from a soft, pliable material enabling said open pouch mouth to be opened to a readily applicable distance for providing access to said pouch interior for easily placing said post drainage container within said pouch interior;
   said back pouch sidewall being turned onto itself to define a loop for receiving a belt and said pouch extension forms the front portion of said loop; and
   said back pouch sidewall being attached to itself after defining said loop at a position beneath said pouch lip so that said pouch lip is unrestricted enabling said pouch extension to deflect into a generally angular position for extending the front of said pouch lip away from said patient.

2. The drainage system of claim 1 wherein said front pouch sidewall terminates at a pouch lip which is interconnected with said pouch extension at first and second lip attachment points, said pouch lip in combination with said pouch extension area forming said open pouch mouth.

3. The drainage system of claim 2 wherein said pouch mouth has a first open position of a generally small width defined by said pouch lip extending across said back pouch sidewall and said pouch extension extending generally vertical above said pouch lip, said pouch mouth also having a second open position wherein said first and second lip attachment points extend outwardly away from said patient deforming said pouch extension to a generally oblique angular position, said deformed pouch extension extending said front pouch sidewall away from said patient thereby fully exposing said pouch interior providing easy access for placing said drainage container within said pouch interior.

4. The drainage system of claim 2 wherein said pouch is made from terry cloth providing said pouch with a soft, light-weight texture for comfort.

* * * * *